(12) United States Patent
Roques et al.

(10) Patent No.: US 6,716,852 B2
(45) Date of Patent: Apr. 6, 2004

(54) AMINO ACID DERIVATIVES AND USE THEREOF AS NEP, ACE AND ECE INHIBITORS

(75) Inventors: Bernard P. Roques, Paris (FR); Marie-Claude Fournie-Zaluski, Paris (FR); Nicolas Inguimbert, Cachan (FR); Hervé Poras, Alfortville (FR); Elizabeth Scalbert, Paris (FR); Caroline Bennejean, Charenton le Pont (FR); Pierre Renard, Le Chesnay (FR)

(73) Assignees: Les Laboratories Servier, Courbevoie Cedex (FR); Institut National de la Recherche Medicale, Paris Cedex (FR)

( * ) Notice: Subject to any disclaimer, the term of this patent is extended or adjusted under 35 U.S.C. 154(b) by 22 days.

(21) Appl. No.: 10/203,704

(22) PCT Filed: Feb. 16, 2001

(86) PCT No.: PCT/FR01/00463
§ 371 (c)(1),
(2), (4) Date: Aug. 12, 2002

(87) PCT Pub. No.: WO01/60822
PCT Pub. Date: Aug. 23, 2001

(65) Prior Publication Data
US 2003/0055086 A1 Mar. 20, 2003

(30) Foreign Application Priority Data
Feb. 17, 2000 (FR) .............................................. 00 01937

(51) Int. Cl.[7] ................... A61K 31/435; A61K 31/405; C07D 209/20; C07D 471/04
(52) U.S. Cl. ...................... 514/292; 514/300; 514/419; 546/84; 546/113; 548/496
(58) Field of Search ........................... 548/496; 546/84, 546/113; 514/292, 300, 419

(56) References Cited

FOREIGN PATENT DOCUMENTS

| EP | 0 449523 A1 | * | 10/1991 |
|---|---|---|---|
| WO | WO 97/24341 | * | 7/1997 |
| WO | WO 97/32874 | * | 9/1997 |

* cited by examiner

*Primary Examiner*—Bernard Dentz
(74) *Attorney, Agent, or Firm*—The Firm of Hueschen and Sage

(57) ABSTRACT

The invention relates to compounds of formula (I):

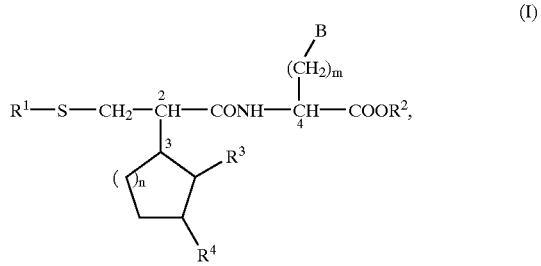

wherein
$0 \leq n \leq 3$,
$0 \leq m \leq 6$,
$R^3$ and $R^4$ together form phenyl,
B represents heteroaryl,
$R^1$ and $R^2$ represent hydrogen or groups as defined in the description.

and medicinal products containing the same which are useful in treating or preventing arterial hypertension and cardiovascular diseases.

26 Claims, No Drawings

AMINO ACID DERIVATIVES AND USE THEREOF AS NEP, ACE AND ECE INHIBITORS

This application is a 371 of PCT/FR01/00463 filed Feb. 16, 2001.

The present invention relates to new N-mercaptoacyl amino acid compounds, to a process for their preparation and to pharmaceutical compositions containing them.

Numerous patent applications describe amino acid compounds for use as inhibitors of neutral endopeptidase (NEP) (EP 449 523), as inhibitors of endothelin converting enzyme (ECE) (WO 97/32874), or as mixed inhibitors of NEP and angiotensin I converting enzyme (ACE).

The pharmacological role played by those enzymes is:
for ACE, to convert angiotensin I to angiotensin II and to degrade bradykinin to inactive peptides,
for NEP, to degrade bradykinin and atrial natriuretic peptide to inactive peptides,
for ECE, to convert big endothelin-1 to endothelin-1.

Angiotensin II, endothelin, bradykinin and atrial natriuretic peptide are the most important peptides hitherto implicated in regulating vascular tone, cardiovascular re-modelling and hydroelectrolytic homeostasis. Their metabolism is essentially controlled by those three enzymes. The inhibition of one and/or the other of those enzymes enables optimum peptidergic balance to be restored by favouring vasodilatory, antitrophic and natriuretic peptides (bradykinin, atrial natriuretic peptide) over vasoconstrictive, trophic and anti-natriuretic peptides (angiotensin II, endothelin-1), hence the cardiovascular therapeutic benefit.

The pharmacological properties of the mixed ACE/NEP inhibitors described in the prior art overlook the major cardiovascular role of the endothelin system (Haynes W. G. et al., Journal of Hypertension, 1998, 16 (8), pp. 1081–1098) and the demonstrated implication of NEP in the degradation of endothelin-1 (Vijayaraghavan J. et al., J. Biol. Chem., 1990, 265, pp. 14150–14155). Thus, treatment with mixed ACE/NEP inhibitors results in an increase in levels of endothelin-1 which, in the long term, can have an adverse effect on the expected therapeutic benefit. This problem is solved by obtaining the three types of inhibition within the same molecule, enabling counter-regulation of that activation and so bringing about sustained strengthened therapeutic efficacy. The development of molecules that inhibit those three enzymes thus constitutes a very significant advance in the treatment of arterial hypertension and cardiovascular diseases.

The compounds of the present invention are new and are excellent triple inhibitors, that is to say they are capable of inhibiting NEP, ACE and ECE simultaneously.

The present invention relates more especially to compounds of formula (I):

$$R^1-S-CH_2-\overset{2}{C}H-CONH-\overset{4}{C}H-COOR^2 \quad \text{with } (CH_2)_m-B \text{ on the CH}, \text{ and cyclopentane ring bearing } R^3, R^4, (\ )_n \tag{I}$$

wherein:
n represents an integer wherein $0 \leq n \leq 3$,
m represents an integer wherein $0 \leq m \leq 6$,
$R^3$ and $R^4$ together form, with the two carbon atoms carrying them, a phenyl group that is unsubstituted or substituted by from 1 to 3 identical or different groups selected from alkyl, alkenyl, alkynyl, alkoxy, hydroxy, alkylthio, mercapto, cyano, nitro, amino, alkylamino, dialkylamino, polyhaloalkyl, azido, carboxy, alkoxycarbonyl, amido, carbamoyl, formyl, acyl, aryl, heteroaryl and halogen atoms,
B represents a heteroaryl group,
$R^2$ represents a hydrogen atom or an alkyl, alkenyl, cycloalkyl, cycloalkylalkyl, acyl, aryl, arylalkyl or aroyl group,
$R^1$ represents a hydrogen atom, an acyl, aroyl or cycloalkylcarbonyl group or a group of formula (II):

$$-S-CH_2-CH-CONH-\overset{}{C}H-COOR^2 \quad \text{with } (CH_2)_m-B, R^3, R^4, (\ )_n \tag{II}$$

wherein m, n, $R^2$, $R^3$, $R^4$ and B are as defined hereinbefore, it being understood that:
"alkyl" is understood to mean an alkyl group having a linear or branched chain containing from 1 to 6 carbon atoms,
"alkenyl" is understood to mean an alkyl group containing from 2 to 6 carbon atoms and one or more double bonds,
"alkynyl" is understood to mean an alkyl group containing from 2 to 6 carbon atoms and one or more triple bonds,
"cycloalkyl" is understood to mean a cyclic alkyl group containing from 3 to 8 carbon atoms,
"acyl" is understood to mean an RCO group wherein R represents an alkyl group as defined hereinbefore,
it being possible for the groups "alkyl", "alkenyl" and "alkynyl" to be substituted by one or more identical or different groups selected from hydroxy, alkoxy, polyhaloalkyl, amino and halogen atoms,
and it being possible for the groups "cycloalkyl" and "cycloalkylalkyl" to be substituted on the cyclic moiety by one or more identical or different groups selected from hydroxy, alkoxy, polyhaloalkyl, amino and halogen atoms,
"aryl" is understood to mean a phenyl or naphthyl group unsubstituted or substituted by one or more identical or different groups selected from alkyl, alkenyl, alkynyl, alkoxy, hydroxy, alkylthio, mercapto, cyano, nitro, amino, alkylamino, dialkylamino, polyhaloalkyl, azido, carboxy, alkoxycarbonyl, amido, carbamoyl, formyl, acyl and halogen atoms,
"heteroaryl" is understood to mean any mono- or poly-cyclic aromatic group containing from 1 to 3 hetero atoms selected from oxygen, sulphur and nitrogen, those groups being unsubstituted or substituted by one or more identical or different groups selected from alkyl, alkenyl, alkynyl, alkoxy, hydroxy, alkylthio, mercapto, cyano, nitro, amino, alkylamino, dialkylamino, polyhaloalkyl, azido, carboxy, alkoxycarbonyl, amido, carbamoyl, formyl, acyl and halogen atoms, it being possible for the polycyclic groups also to be partially or completely hydrogenated on one of the rings,
their enantiomers and diastereoisomers, and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc.

Among the pharmaceutically acceptable bases there may be mentioned by way of non-limiting example sodium hydroxide, potassium hydroxide, triethylamine, tert-butylamine, etc.

The preferred compounds of the invention are the compounds of formula (I) wherein $R^1$ represents a hydrogen atom or an acyl group.

The preferred value for m and n is 1.

The preferred $R^2$ groups are the hydrogen atom and the groups alkyl and arylalkyl.

Advantageously, the invention relates to compounds of formula (I) wherein $R^3$ and $R^4$ together form, with the two carbon atoms carrying them, a substituted phenyl group.

More advantageously, the invention relates to compounds of formula (I) wherein $R^3$ and $R^4$ together form, with the two carbon atoms carrying them, a phenyl group substituted by a halogen atom and more especially by a bromine atom or substituted by an alkoxy or alkylthio group and more especially by the groups methoxy and methylthio.

More advantageously still, the invention relates to compounds of formula (I) substituted in the 2-position by an indane group substituted in the 5-position by a halogen atom and more especially by a bromine atom or by an alkoxy group and more especially by a methoxy group.

The preferred B groups are heteroaryls containing an NH group, such as, for example, the groups indolyl, imidazolyl, pyrrolopyridinyl, pyrroloquinolinyl, pyrrolyl and pyrrolopyrazinyl, more especially the groups indolyl, 1H-pyrrolo[2,3-b]pyridine and 1H-pyrrolo[3,2-h]quinolinyl.

The preferred configuration of the compounds of formula (I) is 2S-3R, and more especially 2S-3R-4S.

More advantageously still, the invention relates to:
N-[2-(5-bromo-2,3-dihydro-1H-inden-1-yl)-3-mercaptopropanoyl]tryptophan,
N-[2-(5-bromo-2,3-dihydro-1H-inden-1-yl)-3-mercaptopropanoyl]tryptophan (2S-3R4S),
N-[2-(5-chloro-2,3-dihydro-1H-inden-1-yl)-3-mercaptopropanoyl]tryptophan,
N-[(2,3-dihydro-1H-inden-1-yl)-3-mercaptopropanoyl]tryptophan,
N-[3-mercapto-2-(1,2,3,4-tetrahydro-1-naphthalenyl)propanoyl]tryptophan,
N-[2-(5-methoxy-2,3-dihydro-1H-inden-1-yl)-3-mercaptopropanoyl]tryptophan,
N-[2-(4-methoxy-2,3-dihydro-1Hinden-1-yl)3-mercaptopropanoyl]tryptophan,
N-[2-(5-ethoxy-2,3-dihydro-1H-inden-1-yl)-3-mercaptopropanoyl]tryptophan,
N-[2-(5-hydroxy-2,3-dihydro-1H-inden-1-yl)-3-mercaptopropanoyl]tryptophan,
N-{2-[5-(methylthio)-2,3-dihydro-1H-inden-1-yl]-3-mercaptopropanoyl}tryptophan,
N-[2-(5-cyano-2,3-dihydro-1H-inden-1-yl)-3-mercaptopropanoyl]tryptophan,
N-[2-(5-bromo-2,3-dihydro-1H-inden-1-yl)-3-mercaptopropanoyl]-3-(1H-pyrrolo-[2,3-b]pyridin-3-yl)alanine,
N-[2-(5-bromo-2,3-dihydro-1H-inden-1-yl)-3-mercaptopropanoyl]-3-(1H-pyrrolo-[2,3-b]pyridin-3-yl)alanine (2S-3R-4S),
N-[2-(5-bromo-2,3-dihydro-1H-inden-1-yl)-3-mercaptopropanoyl]-11-methyltryptophan,
3-(1-benzothiophen-3-yl)-N-[2-(5-bromo-2,3-dihydro-1H-inden-1-yl)-3-mercaptopropanoyl]alanine,
N-[2-(5-bromo-2,3-dihydro-1H-inden-1-yl)-3-mercaptopropanoyl]-3-(3-pyridinyl)alanine,
N-[2-(5-bromo-2,3-dihydro-1H-inden-1-yl)-3-mercaptopropanoyl]-3-(2-quinolinyl)alanine,
N-[2-(5-bromo-2,3-dihydro-1H-inden-1-yl)-3-mercaptopropanoyl]-5-methoxytryptophan (2S-3R-4S),
N-[2-(5-bromo-2,3-dihydro-1H-inden-1-yl)-3-mercaptopropanoyl]-5-fluorotryptophan (2S-3R-4S),
N-[2-(5-bromo-2,3-dihydro-1H-inden-1-yl)-3-mercaptopropanoyl]-3-(1H-pyrrolo[3,2-h]-quinolin-3-yl)alanine (2S-3R-4S).

The present invention relates also to a process for the preparation of compounds of formula (I), characterised in that there is used as starting material a compound of formula (III):

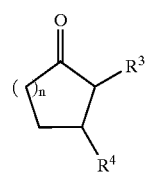

(III)

wherein $R^3$, $R^4$ and n are as defined for formula (I), which is subjected to the action of a reducing agent, such as $NaBH_4$ for example, to obtain a compound of formula (IV):

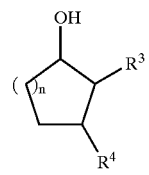

(IV)

wherein n, $R^3$ and $R^4$ are as defined hereinbefore, which is converted with a halogenating agent, such as Me₃SiBr for example, to the corresponding halogen compound of formula (V):

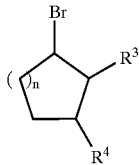
(V)

wherein R³, R⁴ and n are as defined hereinbefore,
which is condensed, in a basic medium, with ethyl 2-(diethoxyphosphoryl)acetate to yield a compound of formula (VI):

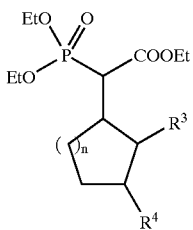
(VI)

wherein R³, R⁴ and n are as defined hereinbefore,
which is reacted with formaldehyde in a basic medium to obtain a compound of formula (VII):

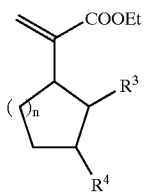
(VII)

wherein R³, R⁴ and n are as defined hereinbefore,
which is hydrolysed in the presence of sodium hydroxide to yield a compound of formula (VIII):

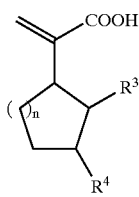
(VIII)

wherein R³, R⁴ and n are as defined hereinbefore,
which is condensed with a compound of formula (IX):

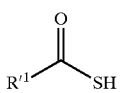
(IX)

wherein $R'^1$ represents an alkyl, aryl or cycloalkyl group, to obtain a compound of formula (X):

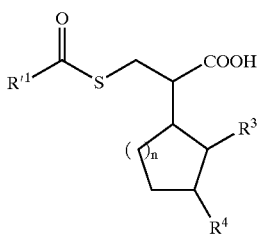
(X)

wherein R³, R⁴, $R'^1$ and n are as defined hereinbefore,
which is condensed, in the presence of a coupling agent, such as 1-(3-dimethylaminopropyl)-3-ethylcarbodiimide for example, with a compound of formula (XI):

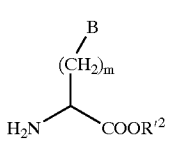
(XI)

wherein B and m are as defined for formula (I), and $R^{12}$ represents an alkyl, alkenyl, cycloalkyl, cycloalkylalkyl, aryl, acyl, arylalkyl or aroyl group,
to yield a compound of formula (I/a), a particular case of the compounds of formula (I):

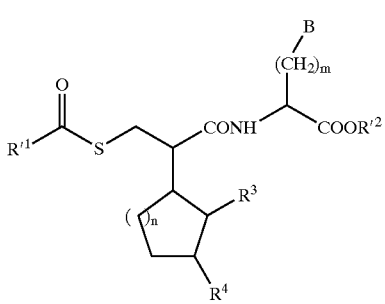
(I/a)

wherein $R'^1$, R³, R⁴, $R'^2$, m, n and B are as defined hereinbefore,
which may be partially or completely hydrolysed in a basic medium to yield a compound of formula (I/b), a particular case of the compounds of formula (I):

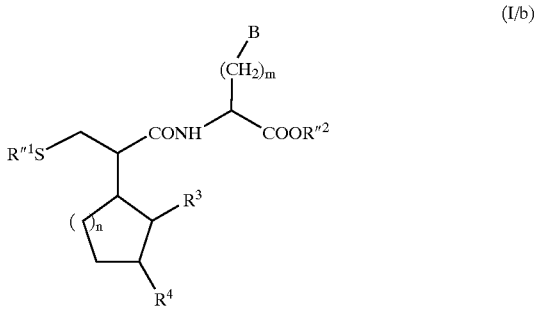
(I/b)

wherein R³, R⁴, m, n and B are as defined hereinbefore, $R''^1$ represents a group $R'^1$ or a hydrogen atom, and $R''^2$ represents a group $R'^2$ or a hydrogen atom, with the proviso that at least one of the groups $R''^1$ and $R''^2$ represents a hydrogen atom, which compound of formula (I/b), when R‴¹ represents a hydrogen atom, may be placed in an oxidising medium to obtain a compound of formula (I/c), a particular case of the compounds of formula (I):

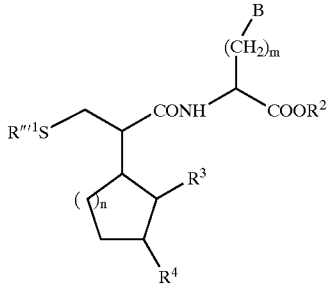

(I/c)

wherein $R^2$, $R^3$, $R^4$, m, n and B are as defined hereinbefore, and $R'''^1$ represents a group of formula (II), which compounds of formulae (I/a) to (I/c) constitute the totality of the compounds of the invention, and may be purified in accordance with a conventional separation technique, are converted, if desired, into addition salts thereof with a pharmaceutically acceptable acid or base, and which are separated, where appropriate, into their isomers in accordance with a conventional separation technique.

The present invention relates also to a process for the preparation of compounds of formula (I), characterised in that there is used as starting material a compound of formula (X) as defined hereinbefore, the diastereoisomers of which are separated by chromatography to yield the compounds of formulae (Xa) and (Xb):

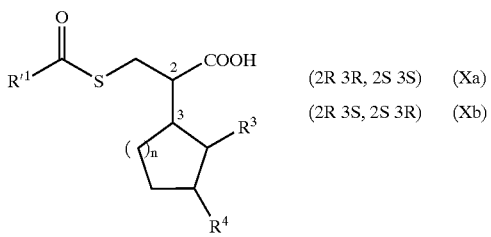

(2R 3R, 2S 3S) (Xa)
(2R 3S, 2S 3R) (Xb)

wherein $R'^1$, $R^3$, $R^4$ and n are as defined hereinbefore, with which compound of formula (Xb) it is possible to form a salt with a chiral amine, such as (R)-(+)-α-methylbenzylamine for example, to yield, after resolution by successive recrystallisation operations, a compound of formula (Xb')

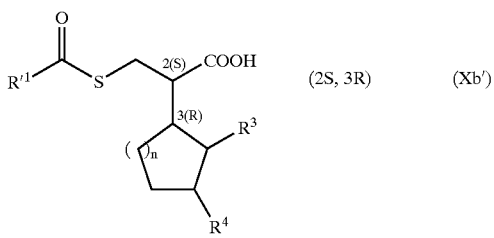

(2S, 3R) (Xb')

wherein $R'^1$, $R^3$, $R^4$ and n are as defined hereinbefore, which is condensed, in the presence of a coupling agent such as EDCI, with a compound of formula (XIa):

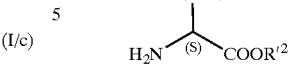

(XIa)

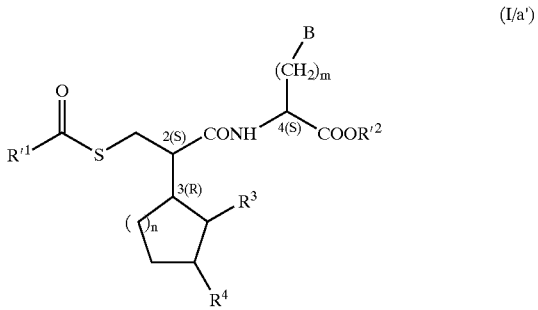

wherein $R'^2$, m and B are as defined hereinbefore, to obtain a compound of formula (I/a'), a particular case of the compounds of formula (I/a):

(I/a')

wherein $R'^1$, $R'^2$, $R^3$, $R^4$, m, n and B are as defined hereinbefore, the diastereoisomers (2R, 3S), (2R, 3R) and (2S, 3R) being obtained analogously starting from the corresponding compounds (Xa) and (Xb), it also being possible to obtain those compounds by condensing a compound of formula (XIa) with a compound of formula (Xa) or (Xb) followed by separation by chromatography.

The compounds of formula (III) are either commercially available or are readily accessible to the person skilled in the art by conventional chemical reactions.

The compounds of the present invention have very valuable pharmacological properties since they enable simultaneous inhibition of:

angiotensin I converting enzyme (ACE), which is responsible for converting angiotensin I into angiotensin II and for degrading bradykinin into inactive peptides, neutral endopeptidase (NEP), which is responsible for degrading bradykinin and atrial natriuretic peptide into inactive peptides, and endothelin converting enzyme (ECE), which is responsible for converting big endothelin-1 into endothelin-1.

Those enzymes play a crucial role in establishing the proportions between vasodilatory, antitrophic and natriuretic peptides on the one hand (bradykinin, atrial natriuretic peptide) and vasoconstrictive, trophic and anti-natriuretic peptides on the other hand (angiotensin II, endothelin 1).

Moreover, it has recently been shown that neutral endopeptidase is implicated in the mechanisms of degradation of endothelin-1. The inhibition of one and/or the other of those enzymes makes it possible to modulate that peptidergic balance.

The numerous mixed ACE/NEP inhibitors described in the literature thus increase the proportion of vasodilatory peptides over vasoconstrictive peptides. Nonetheless, this approach overlooks the role played by the endothelin system, which is all the more harmful because those mixed inhibitors, by inhibiting NEP, increase the levels of endothelin-1, which translates into a reduction in the expected therapeutic benefit.

Triple inhibition avoids the accumulation of endothelin-1, and thus results in sustained strengthened therapeutic efficacy, and in a broadening of the spectrum of activity of the compounds.

Those properties mean that they can be used therapeutically in the treatment of arterial hypertension including pulmonary arterial hypertension, myocardial ischaemia, angina pectoris, cardiac insufficiency, vasculopathies including diabetic vasculopathies, atherosclerosis and post-angioplasty restenosis, acute or chronic renal insufficiency, cerebrovascular diseases including stroke and sub-arachnoidal haemorrhage, peripheral ischaemia, and toxicity to cyclosporin.

The present invention relates also to pharmaceutical compositions comprising at least one compound of formula (I) alone or in combination with one or more pharmaceutically acceptable excipients.

Among the pharmaceutical compositions according to the invention, there may be mentioned more especially those that are suitable for oral, parenteral, nasal, per- or transcutaneous, rectal, perlingual, ocular or respiratory administration and, for example, tablets or dragees, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication, and any associated treatments and ranges from 0.1 mg to 1 g per 24 hours in one or more administrations.

The following Examples illustrate the invention and do not limit it in any way. The following Preparations yield compounds of the invention or synthesis intermediates for use in the preparation of the invention.

Preparation 1: 5-Bromo-1-indanone

Step A: 1-(4-Bromophenyl)-3-chloro-1-propanone 45.3 g of aluminium chloride are stirred at room temperature in 80 ml of $CH_2Cl_2$. Maintaining vigorous stirring, a solution of β-propionic acid chloride (38.09 g, 28.7 ml, 0.3 mol) is poured slowly into 20 ml of $CH_2Cl_2$. The $CH_2Cl_2$-$AlCl_3$-acid chloride complex forms quickly and the solution turns dark red. A solution of bromobenzene (47.1 g, 31.6 ml, 0.3 mol) is then introduced dropwise into 20 ml of $CH_2Cl_2$. The solution is then stirred for 15 hours at room temperature. The mixture is hydrolysed over 190 g of ice, to which 7.6 ml of concentrated acetic acid have been added. The organic phase is washed neutral and the solvent is removed by evaporation under reduced pressure. A dark red oil is obtained, from which the title compound is obtained in the form of a yellowish solid by extraction while hot with petroleum ether.

Melting point: 60–61° C.

Step B: 5-Bromo-1-indanone

A mixture of 448 g of $AlCl_3$ (335.98 mmol) and 112 g of NaCl is brought to 180° C. in a reactor. The mixture is stirred whilst introducing the compound obtained in Step A (44.77 g, 180.9 mmol) slowly using a spatula. The temperature is maintained at 180–220° C. The reaction continues for 30 minutes. Hydrolysis over 4.5 kg of ice in the presence of 135 ml of acetic acid yields a dark brown precipitate, which is filtered off, washed with water and dried in vacuo. The title compound is isolated by recrystallisation from methanol.

Melting point: 126–127° C.

Preparation 2: 1-Oxo-5-indanecarbonitrile

A mixture of 5 g of the compound obtained in Preparation 1 (23 mmol) and 2.65 g of CuCN in 6 ml of DMF is refluxed under argon. After stirring at 120° C. for 15 hours, the mixture is added to a solution of 11.2 g of $FeCl_3$ in 35 ml of water and 6 ml of concentrated hydrochloric acid. The mixture is maintained at 60–71° C. for 15 minutes. The mixture is extracted with 3×20 ml of 10% $NaHCO_3$, dried over $Na_2SO_4$ and concentrated in vacuo to yield the title compound in the form of a slightly yellow solid.

Melting point: 129–130° C.

Preparation 3: 5-(Methylthio)-1-indanone 1.27 g of $CH_3SNa$ (18.13 mmol; 1.2 eq.) are placed in 30 ml of DMF at 0° C. The compound obtained in Preparation 1 (3.19 g; 15.11 mmol) is introduced and the mixture is stirred at room temperature for 3 hours. The reaction mixture is then poured into 150 ml of water and extracted with AcOEt. The organic phase is dried over $Na_2SO_4$ and concentrated in vacuo to yield the title compound in the form of a brownish crystalline product. Melting point: 99–102° C.

Preparation 4: 5-Hydroxy-1-indanone 5 g of 5-methoxy-1-indanone (30.9 mmol) are added under argon to a suspension of 10.31 g of aluminium chloride in 150 ml of anhydrous toluene. The suspension is stirred vigorously whilst being brought to reflux. After reacting for 30 minutes, the mixture is left to return to room temperature, and 30 g of ice are added. The organic phase is separated off. The aqueous phase is washed with 2×30 ml of ethyl acetate. The organic phases are combined, washed with 4×50 ml of water, dried over $Na_2SO_4$ and concentrated in vacuo to yield the title compound in the form of a slightly brown solid.

Melting point: 183° C.

Preparation 5: 5-Ethoxy-1-indanone 3 g of the compound obtained in Preparation 4 (20.2 mmol), 5 ml of ethyl iodide and 8.4 g of potassium carbonate in 200 ml of acetone are refluxed with stirring. After reacting for three hours, the suspension is filtered, and the precipitate is washed with acetone. The acetone is eliminated under reduced pressure. The solid residue is taken up in 25 ml of chloroform, washed with 2×10 ml of water, predried with a saturated sodium chloride solution, filtered over $Na_2SO_4$, and concentrated in vacuo. The title compound is obtained in the form of a slightly orange solid.

Melting point: 82–83° C.

Preparation 6: 5-Chloro-1-indanone

The procedure is as for Preparation 1 starting from chlorobenzene.

Preparation 7: 5-(Dimethylamino)-1-indanone

Step A: N-(2,3-Dihydro-1H-inden-5-yl)acetamide

A mixture of 70 ml of acetic anhydride and 15 g of sodium acetate is added dropwise, with stirring, to 50 g of-5-aminoindane. At the end of the exothermic reaction, the solution is heated at 100° C. for one hour. The solution is then poured into 500 g of ice; a precipitate is observed to form, which is collected by filtration and taken up in 400 ml of ethyl acetate. The solution is washed with 2×250 ml of water, 2×200 ml of a 20% sodium hydrogen carbonate solution, dried over $Na_2SO_4$ and concentrated in vacuo. The title compound is obtained in the form of a yellow solid.

Melting point: 105–106° C.

Step B: N-(1-Oxo-2,3-dihydro-1H-inden-5-yl)acetamide

A solution of 50 g of chromium trioxide dissolved in a mixture of 35 ml of water and 150 ml of acetic acid is added dropwise, with stirring, to 62 g of the compound obtained in Step A in a mixture of 175 ml of acetic acid and 50 ml of acetic anhydride in such a manner that the reaction mixture remains at a temperature below 10° C. After a night at room temperature, the solution is poured into 1 liter of ice-cold water. A precipitate is observed to form, which is collected by filtration. The precipitate is washed with water until neutral and then dried in a dessicator to yield the title compound in the form of a yellow solid.

Melting point: 172° C.

Step C: 5-Amino-1-indanone 47 g of the compound obtained in Step B dissolved in 700 ml of 1.5N hydrochloric acid are brought to reflux. After reacting for one hour, the starting material having passed completely into solution, the solution is left to return to room temperature. The reaction mixture is poured into 800 ml of a 2M sodium hydroxide solution. The precipitate is filtered off and washed with water until neutral to yield the title compound in the form of a yellow solid.

Melting point: 184° C.

Step D: 5-(Dimethylamino)-1-indanone 5 g of the compound obtained in Step C (20.2 mmol), 8.1 ml of methyl iodide and 7.2 g of sodium carbonate in 30 ml of acetone are brought to reflux with stirring. After one night, the solvent is removed in vacuo, yielding a solid which is taken up in a mixture of 100 ml of ethyl acetate and 50 ml of water. The organic phase is separated off, washed with 4×50 ml of water, and then with 50 ml of a saturated sodium chloride solution, dried over $Na_2SO_4$, and concentrated in vacuo. A slightly orange crystalline product is obtained, which is purified by chromatography over neutral alumina.

Melting point: 16° C.

EXAMPLE 1

Methyl 2-{[3-(acetylthio)-2-(5-bromo-2,3-dihydro-1H-inden-1-yl)propanoyl]amino}-3-(1H-indol-3-yl)propanoate Step A: 5-Bromo-1-indanol The compound obtained in Preparation 1 (72.99 mmol) is suspended in 380 ml of MeOH, and sodium borohydride (145.97 mmol, 5.54 g) is added in portions at room temperature. As soon as the highly exothermic reaction has commenced, the temperature is controlled using an ice bath (T<40° C.). The reaction mixture is then stirred for 4 hours at room temperature, 60 ml of water are added, and concentration under reduced pressure is carried out. 100 ml of water are added to the resulting oil, which is extracted with 1×200 ml of AcOEt. The organic phase is separated off, washed with saturated NaCl, dried over $Na_2SO_4$ and then concentrated under reduced pressure to yield the title compound in the form of an oil that crystallises.

Melting point: 79–80° C.

Step B: 1,5-Dibromoindane

The compound obtained in Step A (70.19 mmol) is brought into solution in 420 ml of $CHCl_3$, and bromotrimethylsilane (13.90 ml, 105.28 mmol, 1.5 eq.) is added at room temperature. The reaction mixture is stirred overnight at room temperature. The solvent and excess bromotrimethylsilane are removed by evaporation under reduced pressure. The oil is taken up in 150 ml of $CHCl_3$, washed with 2×80 ml of water and 3×100 ml of saturated NaCl and dried over $Na_2SO_4$. The organic phase is then concentrated under reduced pressure to yield the title compound in the form of a brown oil.

Step C: Ethyl 2-(5-bromo-2,3-dihydro-1H-inden-1-yl)-2-(diethoxyphosphoryl)acetate Triethyl phosphonoacetate (15.47 g, 13.63 ml, 69.06 mmol) is brought into solution, at 0° C. under argon, in 345 ml of degassed DMF, and then 60% NaH (3.04 g, 75.97 mmol, 1.1 eq.) is added in small amounts. The reaction mixture is stirred for 30 minutes at room temperature and the compound obtained in Step B (69.06 mmol) is added all at once. The mixture is stirred overnight at room temperature. The solvent is evaporated under reduced pressure and the residue is taken up in 150 ml of water and extracted with 2×200 ml of AcOEt. The organic phase is washed with water (2×100 ml), saturated NaCl (2×150 ml), dried over $Na_2SO_4$ and then concentrated under reduced pressure to yield the title compound in the form of an oil.

Step D: Ethyl 2-(5-bromo-2,3-dihydro-1H-inden-1-yl)acrylate

The compound obtained in Step C (76.18 mmol), paraformaldehyde (4.60 g, 152.36 mmol, 2 eq.), and $K_2CO_3$ (20.98 g, 2 eq.) are refluxed in 350 ml of THF for 15 hours. The mixture is concentrated to three quarters, 100 ml of water are added and the mixture is extracted with ether. The organic phase is washed with water, with saturated NaCl, dried over $Na_2SO_4$ and then concentrated under reduced pressure to yield the title compound in the form of an oil.

Step E: 2-(5-Bromo-2,3-dihydro-1H-inden-1-yl)acrylic Acid

The ester obtained in Step D (76.18 mmol) and 57.1 ml of 2N sodium hydroxide (114.27 mmol, 1.5 eq.) are stirred in 240 ml of acetone at room temperature for 24 hours. The solvents are removed by evaporation and the residue is taken up in water. The aqueous phase is extracted with ether and then rendered acidic with 3N HCl and finally extracted with ether. The organic phase is washed with water, with saturated NaCl, dried over $Na_2SO_4$ and then concentrated under reduced pressure to yield the title acid.

Step F: 3-(Acetylthio)-2-(5-bromo-2,3-dihydro-1H-inden-1-yl)propanoic Acid

The ethylene compound obtained in Step E (48.83 mmol) is dissolved in 100 ml of $CHCl_3$ and thioacetic acid (170.89 mmol, 3.5 eq.) is added. The mixture is stirred at reflux for 16 hours. The solvent and excess thioacetic acid are removed by evaporation under reduced pressure to yield the title compound in the form of four stereoisomers that can be separated into two enantiomer pairs:

by HPLC chromatography:
HPLC Kromasil C18 5 $\mu$ 100A, 250×4.6 mm, $CH_3CN$—$H_2O$ (0.05% TFA) 60-40
$R_t$ (2S-3S/2R-3R)=11.44 min
$R_t$ (2S-3R/2R-3S)=12.05 min
ESI mass: 343–345 ($MH^+$)

by resolution with a chiral amine:
8.36 g (24.37 mmol) of the resulting mixture are brought into solution in 50 ml of $Et_2O$, and then R(+)-($\alpha$)-methylbenzylamine.(1.05 eq., 25.59 mmol, 3.30 ml) is added. The mixture is placed in a cold chamber at 4° C. for 7 days. The precipitate is collected in suspension in ether and 2N HCl is added until a pH of 1 is obtained. The organic phase is washed with water and then dried over $Na_2SO_4$, to obtain the (2S-3R) isomer.

Step G: Methyl 2-{[3-(acetylthio)-2-(5-bromo-2,3-dihydro-1H-inden-1-yl)propanoyl]amino}-3-(1H-indol-3-yl)propanoate General procedure applicable to the mixture of the four diastereoisomers or to enantiomer pairs:

The compound obtained in Step F (mixture or enantiomer pairs) (100 mg) is dissolved in 2 ml of a THF-$CHCl_3$ mixture, 1-1. To that solution there are added 1.5 eq. of EDCl, 1.5 eq. of HOBT, 1.5 eq. of $Et_3N$ and 1.5 eq. of (L)tryptophan methyl ester hydrohydrochloride. The resulting mixture is stirred at room temperature for 4 hours. The solvents are removed under reduced pressure. The residue is taken up in 15 ml of ethyl acetate, and the organic phase is washed with 3×10 ml of a 10% sodium hydrogen carbonate solution, with 3×10 ml of a 10% citric acid solution, and with 3×10 ml of a saturated sodium chloride solution, dried over $Na_2SO_4$ and concentrated in vacuo.

Example 1a) $2S-3S-4S$
Example 1b) $2R-3R-4R$ } Oil, isolated by *HPLC* chromatography Example 1c) $2S-3R-4S$
Example 1d) $2R-3S-4S$ } Oil, isolated by *HPLC* chromatography

EXAMPLE 2

Methyl 2-{[3-(acetylthio)-2-(5-cyano-2,3-dihydro-1H-inden-1-yl)propanoyl]amino}-3-(1H-indol-3-yl)propanoate The procedure is as for Example 1 starting from the compound obtained in Preparation 2. The last step is carried out on the mixture of the four diastereoisomers.

Oil.

EXAMPLE 3

Methyl 2-{[3-(acetylthio)-2-(5-methylthio-2,3-dihydro-1H-inden-1-yl)propanoyl]amino}-3-(1H-indol-3-yl)propanoate Step A: 5-Methylthio-1-indanol The procedure is as for Step A of Example 1 starting from the compound obtained in Preparation 3.

Step B: Ethyl 2-(5-methylthio-2,3-dihydro-1H-inden-1-yl)-2-(diethoxyphosphoryl)acetate 22 mmol of bromotrimethylsilane are added, with stirring under argon, to a solution of 20 mmol of the compound obtained in Step A in 50 ml of anhydrous THF at −78° C. The temperature of the mixture is left to rise to −20° C. That solution.isadded-to a solution of the triethyl phosphonoacetate anion produced by the action of sodium hydride (20 mmol) on triethyl phosphonoacetate (22 mmol). After a night at room temperature, the solvent is removed and the residue is purified by chromatography over silica. The title compound is obtained in the form of an oil.

Step C: Methyl 2-{[3-(acetylthio)-2-(5-methylthio-2,3-dihydro-1H-inden-1-yl)propanoyl]amino}-3-(1H-indol-3-yl)propanoate The procedure is as for Steps D, E, F and G of Example 1. The last step is carried out on the mixture of the four diastereoisomers.

Oil.

EXAMPLE 4

Methyl 2-{[3-(acetylthio)-2-(5-methoxy-2,3-dihydro-1H-inden-1-yl)propanoyl]amino}-3-(1H-indol-3-yl)propanoate The procedure is as for Example 3 starting from 5-methoxy-1-indanone. The last step is carried out on the mixture of the four diastereoisomers.

Oil.

EXAMPLE 5

Methyl 2-{[3-(acetylthio)-2-(4-methoxy-2,3-dihydro-1H-inden-1-yl)propanoyl]amino}-3-(1H-indol-3-yl)propanoate The procedure is as for Example 1 starting from 4-methoxy-1-indanone. The last step is carried out on the mixture of the four diastereoisomers.

Oil.

EXAMPLE 6

Methyl 2-{[3-(acetylthio)-2-(6-methoxy-2,3-dihydro-1H-inden-1-yl)propanoyl]amino}-3-(1H-indol-3-yl)propanoate The procedure is as for Example 3 starting from 6-methoxy-1-indanone. The last step is carried out on the mixture of the four diastercoisomers.

Oil.

EXAMPLE 7

Methyl 2-{[3-(acetylthio)-2-(5-hydroxy-2,3-dihydro-1H-inden-1-yl)propanoyl]amino}-3-(1H-indol-3-yl)propanoate Step A: 3-(Acetylthio)-2-(5-hydroxy-2,3-dihydro-1H-inden-1-yl)propanoic Acid The compound obtained in Step F of Example 1 (mixture of the four diastercoisomers) (0.4 g, 1.4 mmol) is dissolved in 3 ml of $CH_2Cl_2$ and the resulting solution is cooled to 0° C. 1.3 ml of a 1 M solution of boron tribromide in $CH_2Cl_2$ are added to the mixture. After stirring for 15 minutes at room temperature, the mixture is kept at 40° C. for 30 minutes. The solution is then hydrolysed with 6 ml of water, and then rendered acidic with 2 ml of 1N HCl. The solution is extracted with 2×15 ml of ether. The organic phases are combined, washed twice with 20 ml of water and then predried with 15 ml of a saturated sodium chloride solution, and dried over $Na_2SO_4$ and then concentrated in vacuo, to obtain an oil, which is purified by semi-preparative HPLC.

Step B: Methyl 2-{[3-(acetylthio)-2-(5-hydroxy-2,3-dihydro-1H-inden-1-yl)propanoyl]amino}-3-(1H-indol-3-yl)propanoate The procedure is as for Step G of Example 1. The last step is carried out on the mixture of the four diastereoisomers.

Oil.

EXAMPLE 8

Methyl 2-{[3-(acetylthio)-2-(5-ethoxy-2,3-dihydro-1H-inden-1-yl)propanoyl]amino}-3-(1H-indol-3-yl)propanoate The procedure is as for Example 3 starting from the compound obtained in Preparation 5. The last step is carried out on the mixture of the four diastercoisomers.

Oil.

EXAMPLE 9

Methyl 2-{[3-(acetylthio)-2-(5-chloro-2,3-dihydro-1H-inden-1-yl)propanoyl]amino}-3-(1H-indol-3-yl)propanoate The procedure is as for Example 1 starting from the compound obtained in Preparation 6. The last step is carried out on the mixture of the four diastereoisomers.

Oil.

EXAMPLE 10

Methyl 2-{[3-(acetylthio)-2-(5-dimethylamino-2,3-dihydro-1H-inden-1-yl)propanoyl]amino}-3-(1H-indol-3-yl)propanoate The procedure is as for Example 3 starting from the compound obtained in Preparation 7. The last step is carried out on the mixture of the four diastereoisomers.

Oil.

EXAMPLE 11

Methyl 2-{[3-(acetylthio)-2-(2,3-dihydro-1H-inden-1-yl)propanoyl]-amino}-3-(1H-indol-3-yl)propanoate The procedure is as for Example 1 starting from indanone. The last step is carried out on the mixture of the four diastereoisomers.

Oil.

EXAMPLE 12

Methyl 2-{[3-(acetylthio)-2-(1,2,3,4-tetrahydro-1-naphthalenyl)propanoyl]amino}-3-(1H-indol-3-yl)propanoate The procedure is as for Example 1 starting from 3,4-dihydro-1(2H)-naphthalenone. The last step is carried out on the mixture of the four diastereoisomers.

Oil.

EXAMPLE 13

N-[2-(5-Bromo-2,3-dihydro-1H-inden-1-yl)-3-mercaptopropanoyl]-tryptophan

The compound obtained in Example 1 is dissolved in 2 ml of degassed methanol. After 10 minutes' stirring at room temperature, 6 eq. of a degassed 1M sodium hydroxide solution are added to the solution. The resulting solution is stirred at room temperature under argon. The progress of the reaction is monitored by HPLC. When the reaction is complete, the solution is rendered acidic to pH=I with 1N hydrochloric acid. The methanol is removed in vacuo, 10 ml of water are added to the residue and extraction is carried out with 10 ml of chloroform. The organic phase is dried over $Na_2SO_4$ and concentrated in vacuo.

| | | |
|---|---|---|
| Example 13a): 2S-3S-4S | $[\alpha]_D^{15}$ = +8.80 | |
| | Melting point (decomposition) = 163–165° C. | |
| Example 13b): 2R-3R-4S | $[\alpha]_D^{15}$ = −27.20 | |
| | Melting point (decomposition) = 135–136° C. | |
| Example 13c): 2S-3R-4S | $[\alpha]_D^{15}$ = +20.80 | |
| | Melting point (decomposition) = 126–128° C. | |
| Example 13d): 2R-3S-4S | $[\alpha]_D^{15}$ = −66.80 | |
| | Melting point (decomposition) = 130–132° C. | |

Examples 14 to 24 are obtained by proceeding as for Example 13 starting from the appropriate compounds.

EXAMPLE 14

N-[2-(5-Cyano-2,3-dihydro-ii-inden-1-yl)-3-mercaptopropanoyl]tryptophan

Starting material: Example 2
Solid.
ESI mass: 434 ($MH^+$)

EXAMPLE 15

N-[2-(5-Methylthio-2,3-dihydro-1H-inden-1-yl)-3-mercaptopropanoyl]tryptophan

Starting material: Example 3
Solid.
ESI mass: 455 ($MH^+$)

EXAMPLE 16

N-[2-(5-Methoxy-2,3-dihydro-1H-inden-1-yl)-3-mercaptopropanoyl]tryptophan

Starting material: Example 4
Solid.
ESI mass: 439 ($MH^+$)

EXAMPLE 17

N-[2-(4-Methoxy-2,3-dihydro-1H-inden-1-yl)-3-mercaptopropanoyl]tryptophan

Starting material: Example 5
Solid.
ESI mass: 439 ($MH^+$)

EXAMPLE 18

N-[2-(6-Methoxy-2,3-dihydro-1H-inden-1-yl)-3-mercaptopropanoyl]tryptophan

Starting material: Example 6
Solid.
ESI mass: 439 ($MH^+$)

EXAMPLE 19

N-[2-(5-Hydroxy-2,3-dihydro-1H-inden-1-yl)-3-mercaptopropanoyl]tryptophan

Starting material: Example 7
Solid.
ESI mass: 425 ($MH^+$)

EXAMPLE 20

N-[2-(5-Ethoxy-2,3-dihydro-1H-inden-1-yl)-3-mercaptopropanoyl]tryptophan

Starting material: Example 8
Solid.
ESI mass: 453 ($MH^+$)

EXAMPLE 21

N-[2-(5-Chloro-2,3-dihydro-1H-inden-1-yl)-3-mercaptopropanoyl]tryptophan

Starting material: Example 9
Solid.
ESI mass: 443–445 ($MH^+$)

EXAMPLE 22

N-[2-(5-Dimethylamino-2,3-dilhydro-1H-inden-1-yl)-3-mercaptopropanoyl]tryptophan Starting material: Example 10
Solid.
ESI mass. 452 ($MH^+$)

EXAMPLE 23

N-[2-(2,3-Dihydro-11H-inden-1-yl)-3-mercaptopropanoyl]tryptophan

Starting material: Example 11
Solid.
ESI mass: 409 ($MH^+$)

EXAMPLE 24

N-[2-(1,2,3,4-Tetrahydro-1-naphthalenyl)-3-mercaptopropanoyl]tryptophan

Starting material: Example 12
Solid.
ESI mass: 423 ($MH^+$)

EXAMPLE 25

Methyl 2-{[3-(acetylthio)-2-(5-bromo-2,3-dihydro-1H-inden-1-yl)propanoyl]amino}-3-(2-quinolyl)propanoate The compound obtained in Step F of Example 1 (mixture of the four diastereoisomers) (100 mg) is dissolved in 2 ml of a THF-CHCl$_3$ mixture, 1-1. To that solution there are added 1.5 eq. of EDCI, 1.5 eq. of HOBT, 1.5 eq. of Et$_3$N and 1.5 eq. of methyl (S)-2-amino-3-(2-quinolyl)propanoate. The resulting mixture is stirred at room temperature for 4 hours. The solvents are removed under reduced pressure. The residue is taken up in 15 ml of ethyl acetate, and the organic phase is washed with 3×10 ml of a 10% sodium hydrogen carbonate solution, with 3×10 ml of a 10% citric acid solution, and with 3×10 ml of a saturated sodium chloride solution, dried over Na$_2$SO$_4$ and concentrated in vacuo. The title compound is obtained by HPLC chromatography.

Oil.

EXAMPLE 26

Methyl 2-{[3-(acetylthio)-2-(5-bromo-2,3-dihydro-1H-inden-1-yl)propanoyl]amino}-3-(1-methyl-1H-indol-3-yl)propanoate The procedure is as for Example 25, replacing methyl (S)-2-amino-3-(2-quinolyl)propanoate by methyl (S)-2-amino-3-(1-methyl-1H-indol-3-yl)propanoate.

Oil.

EXAMPLE 27

Methyl 2-{[3-(acetylthio)-2-(5-bromo-2,3-dihydro-1H-inden-1-yl)propanoyl]amino}-3-(1H-pyrrolo[2,3-b]pyridin-3-yl)propanoate The procedure is as for Example 25 starting from the purified (2R-3S) diastereoisomer of the compound obtained in Step F of Example 1 and replacing methyl (S)-2-amino-3-(2-quinolyl)propanoate by methyl 2-amino-3-(1H-pyrrolo[2,3-b]pyridin-3-yl)propanoate (racemic mixture). The two diastereoisomers obtained are separated by HPLC chromatography: HPLC Kromasil C18 5 µ 100A, 250×4.6 mm, CH$_3$CN—H$_2$O (0.05% TFA) 40-60.

Example 27a) 2R-3S-4S: R$_t$=9.71 min–oil
Example 27b) 2R-3S-4R: R$_t$=12.47 min–oil

EXAMPLE 28

Methyl 2-{[3-(acetylthio)-2-(5-bromo-2,3-dihydro-1H-inden-1-yl)propanoyl]amino}-3-(1-benzothien-3-yl)propanoate The procedure is as for Example 25, replacing methyl (S)-2-amino-3-(2-quinolyl)propanoate by methyl (S)-2-amino-3-(1-benzothien-3-yl)propanoate.

Oil.

EXAMPLE 29

Methyl 2-{[3-(acetylthio)-2-(5-bromo-2,3-dihydro-1H-inden-1-yl)propanoyl]amino}-3-(1H-imidazol-4-yl)propanoate The procedure is as for Example 25, replacing methyl (S)-2-amino-3-(2-quinolyl)propanoate by methyl (S)-2-amino-3-(1H-imidazol-4-yl)propanoate.

EXAMPLE 30

Methyl 2-{[3-(acetylthio)-2-(5-bromo-2,3-dihydro-1H-inden-1-yl)propanoyl]amino}-3-(3-pyridinyl)propanoate The procedure is as for Example 25, replacing methyl (S)-2-amino-3-(2-quinolyl)propanoate by methyl (S)-2-amino-3-(3-pyridinyl)propanoate.

EXAMPLE 31

N-[2-(5-Bromo-2,3-dihydro-1H-inden-1-yl)-3-mercaptopropanoyl]-3-(2-quinolyl)alanine The compound obtained in Example 25 is dissolved in 2 ml of degassed methanol. After 10 minutes' stirring at room temperature, 6 eq. of a degassed 1M sodium hydroxide solution are added to the solution. The resulting solution is stirred at room temperature under argon. The progress of the reaction is monitored by HPLC. When the reaction is complete; the solution is rendered acidic to pHr. 1 with 1N hydrochloric acid. The methanol is removed in vacuo, 10 ml of water are added to the residue and extraction is carried out with 10 ml of chloroform. The organic phase is separated off, dried over Na$_2$SO$_4$, concentrated in vacuo, and purified by HPLC chromatography.

Solid.

ESI mass=499-501 (MH$^+$)

Examples 32 to 36 are obtained by proceeding as for Example 31 starting from the appropriate substrate.

EXAMPLE 32

N-[2-(5-Bromo-2,3-dihydro-1H-inden-1-yl)-3-mercaptopropanoyl]-1-methyltryptophan Starting material: Example 26
Solid.
ESI mass: 501–503 (MH$^+$)

EXAMPLE 33

N-[2-(5-Bromo-2,3-dihydro-1H-inden-1-yl)-3-mercaptopropanoyl]-3-(1H-pyrrolo [2,3-b]pyridin-3-yl)alanine Starting material: Example 27a) or Example 27b)
Solid.
ESI mass: 488–490 (MH$^+$)
Example 33a) 2S-3R-4S: R$_t$=4.99 min
Example 33b) 2S-3R-4R: R$_t$=5.49 min

EXAMPLE 34

3-(1-Benzothien-3-yl)-N-[2-(5-bromo-2,3-dihydro-1H-inden-1-yl)-3-mercaptopropanoyl]alanine Starting material: Example 28
Solid.
ESI mass: 500–502 (MH$^+$)

EXAMPLE 35

N-[2-(5-Bromo-2,3-dihydro-1H-inden-1-yl)-3-mercaptopropanoyl]histidine

Starting material: Example 29
Solid.
ESI mass: 438–440 (MH$^+$)

EXAMPLE 36

N-[2-(5-Bromo-2,3-dihydro-1H-inden-1-yl)-3-mercaptopropanoyl]-3-(3-pyridinyl)alanine Starting material: Example 30
Solid.
ESI mass: 448–450 (MH$^+$)

EXAMPLE 37

Methyl 2-{[3-(acetylthio)-2-(5-bromo-2,3-dihydro-1H-inden-1-yl)propanoyl]amino}-3-(1-trityl-1H-imidazol-4-yl)propanoate The compound obtained in Step F of Example 1 (300 mg) is dissolved in 8 ml of a THF-CHCl$_3$ mixture, 1-1. To that solution there are added 1.5 eq. of EDCI, 1.5 eq. of HOBT, 1.5 eq. of Et$_3$N and 1.5 eq. of methyl (S)-2-amino-3-(1-trityl-1H-imidazol-4-yl)propanoate. The resulting mixture is stirred at room temperature for 4 hours. The solvents are removed under reduced pressure. The residue is taken up in 15 ml of ethyl acetate, and the organic phase is washed with 3×20 ml of a 10% sodium hydrogen carbonate solution, with 3×20 ml of a 10% citric acid solution, and with 3×20 ml of a saturated sodium chloride solution, dried over Na$_2$SO$_4$, concentrated in vacuo and purified by HPLC chromatography.
Oil.

EXAMPLE 38

N-[2-(5-Bromo-2,3-dihydro-1H-inden-1-yl)-3-mercaptopropanoyl]-1-tritylhistidine

The compound obtained in Example 37 is dissolved in 5 ml of degassed methanol. After 10 minutes' stirring at room temperature, 4 eq. of a degassed 1M sodium hydroxide solution are, added to that solution. The resulting solution is stirred at room temperature under argon for 5 hours. The progress of the reaction is monitored by HPLC. When the reaction is complete, the solution is rendered acidic to pH=1 with 1N hydrochloric acid. The methanol is removed in vacuo, 10 ml of water are added to the residue and extraction is carried out with 10 ml of chloroform. The organic phase is separated off, dried over Na$_2$SO$_4$, concentrated in vacuo and purified by HPLC chromatography.

Solid.

Note: The compound of Example 35 can be obtained starting from the compound of Example 38 according to the following protocol:

The compound obtained in Example 38 is dissolved in 10 ml of a 95/2.5/2.5 mixture of TFA/H$_2$O/ethanedithiol. After 30 minutes' stirring at room temperature under argon, the solvents are removed in vacuo. The product is purified by HPLC.

EXAMPLE 39

Methyl 2-{[3-(acetylthio)-2-(5-bromo-2,3-dihydro-1H-inden-1-yl)propanoyl]amino}-3-(7-methoxy-1H-indol-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(7-methoxy-1H-indol-3-yl)propanoate (racemic mixture). The two diastereoisomers obtained are separated by HPLC chromatography HPLC Kromasil C18 5 $\mu$ 100A, 250×4.6 mm, CH$_3$CN—H$_2$O (0.05% TFA) 70-30.

Example 39a) (1st diastereoisomer): R$_t$=11.72 min–oil
Example 39b) (2nd diastereoisomer): R$_t$=12.28 min–oil

EXAMPLE 40

Methyl 2-{[3-(acetylthio)-2-(5-bromo-2,3-dihydro-1H-inden-1-yl)propanoyl]amino}-3-(5-hydroxy-1H-indol-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(5-hydroxy-1H-indol-3-yl)propanoate (racemic mixture). The two diastereoisomers obtained are separated by HPLC chromatography HPLC Kromasil C18 5 $\mu$ 100A, 250×4.6 mm, CH$_3$CN—H$_2$O (0.05% TFA) 60-40.

Example 40a) (Ist diastereoisomer): R$_t$=9.20 min–oil
Example 40b) (2nd diastereoisomer): R$_t$=9.29 min–oil

EXAMPLE 41

Methyl 2-{[3-(acetylthio)-2-(5-bromo-2,3-dihydro-1H-inden-1-yl)propanoyl]amino}-3-(5-methoxy-1H-indol-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(5-methoxy-1H-indol-3-yl)propanoate (racemic mixture). The two diastereoisomers obtained are separated by HPLC chromatography HPLC Kromasil C18 5 $\mu$ 100A, 250×4.6 mm, CH$_3$CN—H$_2$O (0.05% TFA) 70-30.

Example 41a) (1st diastereoisomer): R$_t$=9.54 min–oil
Example 41b) (2nd diastereoisomer): R$_t$=10.11 min–oil

EXAMPLE 42

Methyl 2-{[3-(acetylthio)-2-(5-bromo-2,3-dihydro-1H-inden-1-yl)propanoyl]amino}-3-(5-bromo-1H-indol-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(5-bromo-1H-indol-3-yl)propanoate (racemic mixture). The two diastereoisomers obtained are separated by HPLC chromatography HPLC Kromasil C18 5 $\mu$ 100A, 250×4.6 mm, CH$_3$CN—H$_2$O (0.05% TFA) 70-30.

Example 42a) (1st diastereoisomer): R$_t$=16.36 min–oil
Example 42b) (2nd diastereoisomer): R$_t$=16.83 min–oil

EXAMPLE 43

Methyl 2-{[3-(acetylthio)-2-(5-bromo-2,3-dihydro-1H-inden-1-yl)propanoyl]amino}-3-(5-methyl-1H-indol-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(5-methyl-1H-indol-3-yl)propanoate (racemic mixture). The two diastereoisomers obtained are separated by HPLC chromatography HPLC Kromasil C18 5μ 100A, 250×4.6 mm, CH$_3$CN—H$_2$O (0.05% TFA) 70-30.

Example 43a) (1st diastereoisomer) R$_t$=14.10 min–oil
Example 43b) (2nd diastereoisomer) R$_t$=14.53 min–oil

EXAMPLE 44

Methyl 2-{[3-(acetylthio)-2-(5-bromo-2,3-dihydro-1H-inden-1-yl)propanoyl]amino}-3-(6-methyl-1H-indol-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(6-methyl-1H-indol-3-yl)propanoate (racemic mixture). The two diastereoisomers obtained are separated by HPLC chromatography HPLC Kromasil C18 5 μ 100A, 250×4.6 mm, CH$_3$CN—H$_2$O (0.05% TFA) 70-30.

Example 44a) (1st diastereoisomer): R$_t$=14.00 min–oil
Example 44b) (2nd diastereoisomer): R$_t$=14.54 min–oil

EXAMPLE 45

Methyl 2-{[3-(acetylthio)-2-(5-bromo-2,3-dihydro-1H-inden-1-yl)propanoyl]amino}-3-(6-fluoro-1H-indol-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(6-fluoro-1H-indol-3-yl)propanoate (racemic mixture). The two diastereoisomers obtained are separated by HPLC chromatography: HPLC Kromasil C18 5 μ 100A, 250×4.6 mm, CH$_3$CN—H$_2$O (0.05% TFA) 60-40.

Example 45a) (1st diastereoisomer): R$_t$=11.09, min–oil
Example 45b) (2nd diastereoisomer): R$_t$=11.90 min–oil

EXAMPLE 46

Methyl 2-{[3-(acetylthio)-2-(5-bromo-2,3-dihydro-1H-inden-1-yl)propanoyl]amino}-3-(5-fluoro-1H-indol-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(5-fluoro-11H-indol-3-yl)propanoate (racemic mixture). The two diastereoisomers obtained are separated by HPLC chromatography HPLC Kromasil C18 5 μ 100A, 250×4.6 mm, CH$_3$CN—H$_2$O (0.05% TFA) 70-30.

Example 46a) (1st diastereoisomer) R$_t$=11.13 min–oil
Example 46b) (2nd diastereoisomer): R$_t$=11.77 min–oil

EXAMPLE 47

Methyl 2-{[3-(acetylthio)-2-(5-bromo-2,3-dihydro-1H-inden-1-yl)propanoyl]amino}-3-(1H-indazol-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(1H-indazol-3-yl)propanoate (racemic mixture). R$_t$ mixture (HPLC Kromasil C18 5 μ 100A, 250×4.6 mm, CH$_3$CN—H$_2$O (0.05% TFA) 70-30)=7.87 min
Oil

EXAMPLE 48

Methyl 2-{[3-(acetylthio)-2-(5-bromo-2,3-dihydro-1H-inden-1-yl)propanoyl]amino}-3-(1H-pyrrolo[2,3-c]pyridin-3-yl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 2-amino-3-(1H-pyrrolo[2,3-c]pyridin-3-yl)propanoate (racemic mixture). The two diastereoisomers obtained are separated by HPLC chromatography: HPLC Kromasil C18 5 μ 100A, 250×4.6 mm, CH$_3$CN—H$_2$O (0.05% TFA) 50-50.

Example 48a) (1st diastereoisomer): R$_t$=4.70 min–oil
Example 48b) (2nd diastereoisomer): R$_t$=5.62 min–oil

EXAMPLE 49

Methyl 2-{[3-(acetylthio)-2-(5-bromo-2,3-dihydro-1H-inden-1-yl)propanoyl]amino}-3-(9-acridinyl)propanoate The procedure is as for Example 25 starting from the purified (2S-3R) diastereoisomer of the compound obtained in Step F of Example 1 and replacing methyl (S)-2-amino-3-(2-quinolyl)propanoate by methyl 3-(9-acridinyl)-2-aminopropanoate (racemic mixture). The two diastereoisomers obtained are separated by HPLC chromatography: HPLC Kromasil C18 5 μ 100A, 250×4.6 mm, CH$_3$CN—H$_2$O (0.05% TFA) 50-50.

Example 49a) (1st diastereoisomer) R$_t$=6.48 min–oil
Example 49b) (2nd diastereoisomer): R$_t$=7.00 min–oil

EXAMPLE 50

Methyl 2-{[3-(acetylthio)-2-(5-bromo-2,3-dihydro-1H-inden-1-yl)propanoyl]amino}-3-(1H-pyrrolo[3,2-4]quinolin-3-yl)propanoate The procedure is as for Example 25 starting from the purified (2S-3R) diastereoisomer of the compound obtained in Step F of Example 1 and methyl (S)-2-amino-3-(2-quinolyl)propanoate by methyl 2-amino-3-(1H-pyrrolo[3,2-h]quinolin-3-yl)propanoate (racemic mixture). The two diastereoisomers obtained are separated by HPLC chromatography: HPLC Kromasil C18 5 μ 100A, 250×4.6 mm, CH$_3$CN—H$_2$O (0.05% TFA) 70-30.

Example 50a) (1st diastereoisomer) R$_t$=3.30 min–oil
Example 50b) (2nd diastereoisomer): R$_t$=3.87 min–oil

EXAMPLE 51

Methyl 2-{[3-(acetylthio)-2-(5-methoxy-2,3-dihydro-1H-inden-1-yl)propanoyl]amino}-3-(5-hydroxy-1H-indol-3-yl)propanoate The procedure is as for Example 1 starting from 5-methoxy-1-indanone and, in Step G, condensing 5-hydroxytryptophan methyl ester hydrochloride with the purified (2S-3R) diastereoisomer of the compound obtained in Step F. The two diastereoisomers obtained are separated by HPLC chromatography: HPLC Kromasil C18 5 μ 100A, 250×4.6 mm, CH$_3$CN—H$_2$O (0.05% TFA) 60-40.

Example 51a) (1st diastereoisomer) R$_t$=5.80 min–oil
Example 51b) (2nd diastereoisomer): R$_t$=6.10 min–oil

EXAMPLE 52

N-[2-(5-Bromo-2,3-dihydro-1H-inden-1-yl)-3-mercaptopropanoyl]-7-methoxytryptophan The procedure is as for Example 13 starting from the compound obtained in Example 39 (mixture). The two diastereoisomers obtained are separated by HPLC chromatography HPLC Kromasil C18 5 μ 100A, 250×4.6 mm, $CH_3CN$—$H_2O$ (0.05% TFA) 70-30.

Example 52a) (1st diastereoisomer) $R_t$=6.57 min–solid

Example 52b) (2nd diastereoisomer): $R_t$=6.16 min–solid ESI mass: 517–519 ($MH^+$)

EXAMPLE 53

N-[2-(5-Bromo-2,3-dihydro-1H-inden-1-yl)-3-mercaptopropanoyl]-5-hydroxytryptophan The procedure is as for Example 13 starting from the compound obtained in Example 40a):

Example 53a) (2S-3R-4S): $R_t$=3.91 min (HPLC Kromasil C18 5 μ 100A, 250×4.6 mm, $CH_3CN$—$H_2O$ (0.05% TFA) 70-30)

Solid—ESI mass: 503–505 ($MH^+$)

EXAMPLE 54

N-[2-(5-Bromo-2,3-dihydro-1H-inden-1-yl)-3-mercaptopropanoyl]-5-methoxytryptophan The procedure is as for Example 13 starting from the compound obtained in Example 41 (mixture). The two diastereoisomers obtained are separated by HPLC chromatography: HPLC Kromasil C18 5 μ 100A, 250×4.6 mm, $CH_3CN$—$H_2O$ (0.05% TFA) 70-30.

Example 54a) (2S-3R-4S): $R_t$=5.55 min–solid–ESI mass: 517–519 ($MH^+$)

Example 54b) (2S-3R-4R): $R_t$=5.77 min–solid–ESI-mass: 517–519 ($MH^+$)

EXAMPLE 55

5-Bromo-N-[2-(5-bromo-2,3-dihydro-1H-inden-1-yl)-3-mercaptopropanoyl]tryptophan

The procedure is as for Example 13 starting from the compound obtained in Example 42 (mixture). The two diastereoisomers obtained are separated by UPLC chromatography HPLC Kromasil C18 5 μ 100A, 250×4.6 mm, $CH_3CN$—$H_2O$ (0.05% TFA) 70-30.

Example 55a) (1st diastereoisomer): $R_t$=7.94 min–solid ESI mass: 565-567-569 ($MH^+$)

Example 55b) (2nd diastereoisomer): $R_t$=8.63 min–solid– ESI mass: 565-567-569 ($MH^+$)

EXAMPLE 56

N-[2-(5-Bromo-2,3-dihydro-1H-inden-1-yl)-3-mercaptopropanoyl]-5-methyltryptophan The procedure is as for Example 13 starting from the compound obtained in Example 43 (mixture). The two diastereoisomers obtained are separated by HPLC chromatography: HPLC Kromasil C18 5 μ 100A, 250×4.6 mm, $CH_3CN$—$H_2O$ (0.05% TFA) 70-30.

Example 56a) (1st diastereoisomer): $R_t$=6.94 min–solid– ESI mass: 501–503 ($MH^+$)

Example 56b) (2nd diastereoisomer): $R_t$=7.42 min–solid– ESI mass: 501–503 ($MH^+$)

EXAMPLE 57

N-[2-(5-Bromo-2,3-dihydro-1H-inden-1-yl)-3-mercaptopropanoyl]-6-methyltryptophan The procedure is as for Example 13 starting from the compound obtained in Example 44 (mixture). The two diastereoisomers obtained are separated by HPLC chromatography HPLC Kromasil C18 5 μ 100A, 250×4.6 mm, $CH_3CN$—$H_2O$ (0.05% TFA) 70-30.

Example 57a) (1st diastereoisomer): $R_t$=7.13 min–solid– ESI mass: 501–503 ($MH^+$)

Example 57b) (2nd diastereoisomer): $R_t$=7.67 min–solid– ESI mass: 501–503 ($MH^+$)

EXAMPLE 58

N-[2-(5-Bromo-2,3-dihydro-1H-inden-1-yl)-3-mercaptopropanoyl]-6-fluorotryptophan The procedure is as for Example 13 starting from the compound obtained in Example 45 (mixture). The two diastereoisomers obtained are separated by HPLC chromatography HPLC Kromasil C18 5 μ 100A, 250×4.6 mm, $CH_3CN$—$H_2O$ (0.05% TFA) 70-30.

Example 58a) (1st diastereoisomer): $R_t$=6.10 min–solid– ESI mass: 505–507 ($MH^+$)

Example 58b) (2nd diastereoisomer): $R_t$=6.40 min–solid– ESI mass: 505–507 ($MH^+$)

EXAMPLE 59

N-[2-(5-Bromo-2,3-dihydro-1H-inden-1-yl)-3-mercaptopropanoyl]-5-fluorotryptophan The procedure is as for Example 13 starting from the compound obtained in Example 46 (mixture). The two diastereoisomers obtained are separated by HPLC chromatography: HPLC Kromasil C18 5 μ 100A, 250×4.6 mm, $CH_3CN$—$H_2O$ (0.05% TFA) 70-30.

Example 59a) (2S-3R-4S): $R_t$=6.09 min–solid–ESI mass: 505–507 ($MH^+$)

Example 59b) (2S-3R-4R): $R_t$=5.99 min–solid–ESI mass: 505–507 ($MH^+$)

EXAMPLE 60

N-[2-(5-Bromo-2,3-dihydro-1H-inden-1-yl)-3-mercaptopropanoyl]-3-(1H-indazol-3-yl)alanine The procedure is as for Example 13 starting from the compound obtained in Example 47 (mixture). The two diastereoisomers obtained are separated by HPLC chromatography HPLC Kromasil C18 5 μ 100A, 250×4.6 mm, $CH_3CN$—$H_2O$ (0.05% TFA) 60-40.

Example 60a) (2S-3R-4S): $R_t$=7.22 min–solid–ESI mass: 488–490 ($MH^+$)

Example 60b) (2S-3R-4R): $R_t$=7.75 min–solid–ESI mass: 488–490 ($MH^+$)

EXAMPLE 61

N-[2-(5-Bromo-2,3-dihydro-1H-inden-1-yl)-3-mercaptopropanoyl]-3-(1H-pyrrolo[2,3-c]pyridin-3-yl)alanine The procedure is as for Example 13 starting from the compound obtained in Example 48 (mixture). The two diastereoisomers obtained are separated by HPLC chromatography: HPLC Kromasil C18 5 μ 100A, 250×4.6 mm, $CH_3CN$—$H_2O$ (0.05% TFA) 50-50.

Example 61a) (1st diastereoisomer): $R_t$=3.35 min–solid– ESI mass: 488–490 ($MH^+$)

Example 61b) (2nd diastereoisomer): $R_t$=3.62 min–solid– ESI mass: 488–490 ($MH^+$)

EXAMPLE 62

3-(9-Acridinyl)-N-[2-(5-bromo-2,3-dihydro-1H-inden-1-yl)-3-mercaptopropanoyl]alanine The procedure is as for Example 13 starting from the compound obtained in Example 49 (mixture).

$R_t$ mixture (HPLC Kromasil C18 5 μ 100A,250×4.6 mm, $CH_3CN—H_2O$ (0.05% TFA) 5(50) 4.02 min Solid–ESI mass: 546–548 (MH+)

EXAMPLE 63

N-[2-(5-Bromo-2,3-dihydro-1H-inden-1-yl)-3-mercaptopropanoyl]-3-(1H-pyrrolo[3,2-h]quinolin-3-yl)alanine The procedure is as for Example 13 starting from the compound obtained in Example 50 (mixture). The two diastereoisomers obtained are separated by HPLC chromatography: HPLC Kromasil C18 5 μ 100A, 250×4.6 mm, $CH_3CN—H_2O$ (0.05% TFA) 60-40.

Example 63a) (2S-3R-4S): $R_t$=3.50 min–solid–ESI mass: 538–540 (MH+)

Example 63b) (2S-3R-4R): $R_t$=3.19 min–solid–ESI mass: 538–540 (MH+)

EXAMPLE 64

5-Hydroxy-N-[3-mercapto-2-(5-methoxy-2,3-dihydro-1H-inden-1-yl)propanoyl]tryptophan The procedure is as for Example 13 starting from the compound obtained in Example 51 (mixture).

$R_t$ mixture (HPLC Kromasi C18 5 μ 100A,250×4.6 mm, $CH3CN—H_2O$ (0.05% TFA) 6040)=4.00 min Solid.

EXAMPLE 65

Methyl 2-{[3-(acetylthio)-2-(5,6-dimethoxy-2,3-dihydro-1H-inden-1-yl)propanoyl]aminol}-3-(5-hydroxy-1H-indol-3-yl)propanoate The procedure is as for Example 1 starting from 5,6-dimethoxy-1-indanone and, in Step G, condensing 5-hydroxytryptophan methyl ester hydrochloride with the compound obtained in Step F (mixture).

Oil.

EXAMPLE 66

N-[2-(5,6-Dimethoxy-2,3-dihydro-1H-inden-1-yl)-3-mercaptopropanoyl]-5-hydroxytryptophan The procedure is as for Example 13 starting from the compound obtained in Example 65 (mixture).

$R_t$ mixture (HPLC Kromasil C18 5 μ 100A, 250×4.6 mm, $CH_3CN—H_2O$ (0.05% TFA) 6040)=5.16 min Solid

Pharmacological Study

EXAMPLE A

Inhibition of Neutral Endopeptidase

Neutral endopeptidase is purified from rabbit kidney according to the procedure described by Aubry et al. (Biochem. Cell Biol., 1987, 65, pp. 1037–1042).

The enzyme activity is measured using the fluorescent substrate, Dansyl-Gly-(p-$NO_2$)Phe-β-Ala-(DGNPA), Km=37 μM (Goudreau N. et al., Anal. Biochem., 1994, 219, pp. 87–95).

The compounds of the invention demonstrate an excellent capacity for inhibiting neutral endopeptidase with Ki values of from 2 to 50 nM.

By way of example, the compounds of Examples 33 (2S-3R-4S), 13 (2S-3R-4S) and 63 (2S-3R-4S) have Ki values of 2.91±0.67 nM, 3.28±0.35 nM and 10.2±0.3 nM, respectively.

EXAMPLE B

Inhibition of Angiotensin I Converting Enzyme

ACE is purified from rat testicle according to the procedure described by Pantaliano et al. (Biochemistry, 1984, 23, pp. 1037–1042).

The enzyme activity is measured using the synthetic substrate N-Cbz-Phe-His-Leu, Km=50 mM (Piquilloud Y. et al., Biochem. Biophys. Acta, 1970, 206, pp. 136–142).

The compounds of the invention demonstrate an excellent capacity for inhibiting angiotensin I converting enzyme with Ki values of from 2 to 50 nM.

By way of example, the compounds of Examples 33 (2S-3R-4S), 13 (2S-3R-4S) and 63 (2S-3R-4S) have Ki values of 1.32±0.17 nM, 4.09±0.49 nM and 3.7±0.38 nM, respectively.

EXAMPLE C

Inhibition of Endothelin (ET) Converting Enzyme

The cDNA of ECE-1c (membrane form of the enzyme, Biochem. J., 1997, 328, pp. 871–877), was inserted into a pcDNA3 eucaryotic expression vector and then transfected by electroporation and expressed in Cos-7 cells.

To measure the ECE activity, the cells are homogenised and the membrane fraction is recovered. The enzyme is extracted by dissolution in β-octylglucose (1%).

a) Synthesis of the Substrate

The peptide BigET-1 (19-35) was prepared by solid phase synthesis in Fmoc chemistry and purified by semi-preparative HPLC. The propionylation of the peptide was effected by the action of N-succinimidyl-[2,3-$^3$H]-propionate on the peptide BigET-1 (19-35) and the radiolabelled product was purified by HPLC. The specific activity of the substrate is 97 Ci/mmole.

b) Enzyme Assay

ECE-1c (10 μl of a solution diluted to ⅒) is dissolved in 400 μl of Trismaleate 50 mM, pH 6.5, in the presence of 250 mM NaCl. The reaction is initiated by the addition of 10 μl of the radioactive substrate (final concentration 1×10$^{-9}$ M). After incubation for 1 hour at 37° C., the reaction is stopped by the addition of 600 μl of ethyl acetate. The metabolite is separated from the intact substrate by liquid—liquid extraction. The radioactivity of the metabolite is determined by liquid scintillation. The kinetic constants of the substrate are: Km=17.1±0.6 zM and Vmax=2.98±0.24 mmol/mg. prot./min.

To determine the Ki values of the inhibitors, the latter are preincubated for 10 minutes at 37° C. at different concentrations (from 10$^{-4}$ to 10$^{-10}$ M) before the addition of the substrate. The controls of 0% and 100% degradation are obtained, respectively, by incubation of the substrate with the inactivated enzyme and with the native enzyme in the absence of inhibitors.

The compounds of the invention demonstrate an excellent capacity for inhibiting big endothelin converting enzyme with Ki values of from 2 to 50 nM.

By way of example, the compounds of Examples 33 (2S-3R-4S), 13 (2S-3R-4S) and 63 (2S-3R-4S) have Ki values of 23.3±3.2 nM, 24.4±1.4 nM and 21.2±2.5 nM, respectively.

EXAMPLE D

Pharmaceutical Composition

| | |
|---|---|
| 1000 tablets containing a dose of 5 mg of N-[2-(5-bromo-2, 3-dihydro-1H-inden-1-yl)-3-mercaptopropanoyl]tryptophan (2S-3R-4S) (Example 13c)) | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

We claim:

1. A compound selected from those of formula (I):

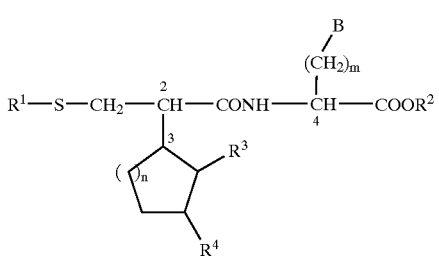

(I)

wherein:

n represents an integer wherein $0 \leq n \leq 3$, m represents an integer wherein $0 \leq m \leq 6$, $R^3$ and $R^4$ together form, with the two carbon atoms carrying them, phenyl which may be unsubstituted or substituted by 1 to 3 identical or different groups selected from alkyl, alkenyl, alkynyl, alkoxy, hydroxy, alkylthio, mercapto, cyano, nitro, amino, alkylamino, dialkylamino, polyhaloalkyl, azido, carboxy, alkoxycarbonyl, amido, carbamoyl, formyl, acyl, aryl, heteroaryl, and halogen, B represents heteroaryl, $R^2$ represents hydrogen, alkyl, alkenyl, cycloalkyl, cycloalkylalkyl, acyl, aryl, arylalkyl, or aroyl, $R^1$ represents hydrogen, acyl, aroyl, cycloalkylcarbonyl, or a group of formula (II):

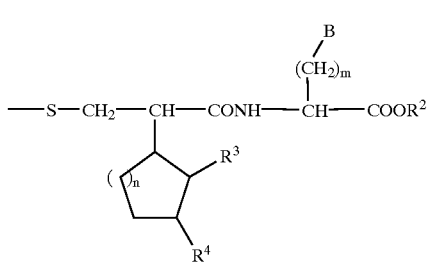

(II)

wherein m, n, $R^2$, $R^3$, $R^4$ and B are as defined hereinbefore, it being understood that:

"alkyl" is a linear or branched, 1 to 6 carbon alkyl group,

"alkenyl" is a 2 to 6 carbon alkyl group with one or more double bonds,

"alkynyl" is a 2 to 6 carbon alkynyl group with one or more triple bonds,

"cycloalkyl" is a 3 to 8 carbon cyclic alkyl group,

"acyl" is a group RCO wherein R represents alkyl as defined hereinbefore, it being possible for the groups "alkyl", "alkenyl" and "alkynyl" to be substituted by one or more identical or different groups selected from hydroxy, alkoxy, polyhaloalkyl, amino, and halogen, and it being possible for the groups "cycloalkyl" and "cycloalkylalkyl" to be substituted on the cyclic moiety by one or more identical or different groups selected from hydroxy, alkoxy, polyhaloalkyl, amino, and halogen, "aryl" may be phenyl or naphthyl, unsubstituted or substituted by one or more identical or different groups selected from alkyl, alkenyl, alkynyl, alkoxy, hydroxy, alkylthio, mercapto, cyano, nitro, amino, alkylamino, dialkylamino, polyhaloalkyl, azido, carboxy, alkoxycarbonyl, amido, carbamoyl, formyl, acyl, and halogen, "heteroaryl" may be any mono- or poly-cyclic aromatic group containing 1 to 3 hetero atoms selected from oxygen, sulphur and nitrogen, the aromatic groups being unsubstituted or substituted by one or more identical or different groups selected from alkyl, alkenyl, alkynyl, alkoxy, hydroxy, alkylthio, mercapto, cyano, nitro, amino, alkylamino, dialkylamino, polyhaloalkyl, azido, carboxy, alkoxycarbonyl, amido, carbamoyl, formyl, acyl, and halogen, it being possible for the polycyclic groups also to be partially or completely hydrogenated on one of the rings, its enantiomers, diastereoisomers, and addition salts thereof with a pharmaceutically-acceptable acid or base.

2. A compound of claim 1 wherein $R^1$ represents hydrogen.

3. A compound of claim 1 wherein $R^1$ represents acyl.

4. A compound of claim 1 wherein $R^2$ represents hydrogen.

5. A compound of claim 1 wherein $R^2$ represents alkyl.

6. A compound of claim 1 wherein $R^3$ and $R^4$ together form a substituted phenyl.

7. A compound of claim 1 wherein $R^3$ and $R^4$ together form phenyl substituted by halogen or by methoxy.

8. A compound of claim 1 wherein n is 1.

9. A compound of claim 1 wherein m is 1.

10. A compound of claim 1 wherein B represents heteroaryl containing NH.

11. A compound of claim 1 wherein B represents indolyl.

12. A compound of claim 1 wherein B represents pyrrolopyridinyl.

13. A compound of claim 1 wherein B represents pyrroloquinolinyl.

14. A compound of claim 1 of configuration 2S-3R.

15. A compound of claim 1 of configuration 2S-3R-4S.

16. A compound of claim 1 which is selected from N[2-(5-bromo-2,3-dihydro-1H-inden-1-yl)-3-mercaptopropanoyl]tryptophan, its enantiomers, diastereoisomers, and addition salts thereof with a pharmaceutically-acceptable acid or base.

17. A compound of claim 1 which is selected from N-[2-(5-bromo-2,3-dihydro-1H-inden-1 -yl)-3-mercaptopropanoyl]tryptophan (2S-3R-4S) and its addition salts thereof with a pharmaceutically-acceptable acid or base.

18. A compound of claim 1 which is selected from N-[2-(5-methylthio-2,3-dihydro-1H-inden-1-yl)-3- mercaptopropanoyl]tryptophan, its enantiomers, diastereoisomers, and addition salts thereof with a pharmaceutically-acceptable acid or base.

19. A compound of claim 1 which is selected from N-[2-(5-methoxy-2,3-dihydro-1H-inden-1-yl)-3-mercaptopropanoyl]tryptophan, its enantiomers, diastereoisomers, and addition salts thereof with a pharmaceutically-acceptable acid or base.

20. A compound of claim 1 which is selected from N-[2-(5-bromo-2,3-dihydro-1H-inden-1-yl)-3-mercaptopropanoyl]-3-(1H-pyrrolo[2,3-b]pyridin-3-yl)alanine, its enantiomers, diastereoisomers, and addition salts thereof with a pharmaceutically-acceptable acid or base.

21. A compound of claim 1 which is selected from N-[2-(5-bromo-2,3-dihydro-1H-inden-1-yl)-3-mercaptopropanoyl]-3-(1H-pyrrolo[2,3-b]pyridin-3-yl)alanine (2S-3R-4S) and its addition salts thereof with a pharmaceutically-acceptable acid or base.

22. A compound of claim 1 which is selected from N-[2-(5-bromo-2,3-dihydro-1H-inden-1-yl)-3-mercaptopropanoyl]-5-methoxytryptophan (2S-3R-4S) and its addition salts thereof with a pharmaceutically-acceptable acid or base.

23. A compound of claim 1 which is selected from N-[2-(5-bromo-2,3-dihydro-1H-inden-1-yl)-3-mercaptopropanoyl]-5-fluorotryptophan (2S-3R-4S) and its addition salts thereof with a pharmaceutically-acceptable acid or base.

24. A compound of claim 1 which is selected from N-[2-(5-bromo-2,3-dihydro-1H-inden-1-yl)-3-mercaptopropanoyl]-3-(1H-pyrrolo[3,2-h]quinolin-3-yl)alanine (2S-3R-4S) and its addition salts thereof with a pharmaceutically-acceptable acid or base.

25. A method for treating a living animal body afflicted with a condition selected from arterial hypertension including pulmonary arterial hypertension, myocardial ischaemia, angina pectoris, cardiac insufficiency, vasculopathies including diabetic vasculopathies, atherosclerosis and angioplasty restenosis, acute or chronic renal insufficiency, cerebrovascular diseases including stroke and sub-arachnoidal haemorrhage, peripheral ischaemia, and toxicity to cyclosporin, comprising the step of administering to the living animal body an amount of a compound of claim 1 which is effective for alleviation of the condition.

26. A pharmaceutical composition useful for treating arterial hypertension including pulmonary arterial hypertension, myocardial ischaemia, angina pectoris, cardiac insufficiency, vasculopathies including diabetic vasculopathies, atherosclerosis and angioplasty restenosis, acute or chronic renal insufficiency, cerebrovascular diseases including stroke and sub-arachnoidal haemorrhage, peripheral ischaemia, and toxicity to cyclosporin, comprising as active principle an effective amount of a compound of claim 1 together with one or more pharmaceutically-acceptable excipients or vehicles.

* * * * *

UNITED STATES PATENT AND TRADEMARK OFFICE
CERTIFICATE OF CORRECTION

PATENT NO. : 6,716,852 B2
APPLICATION NO. : 10/203704
DATED : April 6, 2004
INVENTOR(S) : Bernard P. Roques et al.

It is certified that error appears in the above-identified patent and that said Letters Patent is hereby corrected as shown below:

Cover Page, Assignees: "Les Laboratories Servier" should be
-- Les Laboratoires Servier --.

Signed and Sealed this

Twenty-ninth Day of January, 2008

JON W. DUDAS
*Director of the United States Patent and Trademark Office*